(12) United States Patent
Hamuro

(10) Patent No.: US 11,974,753 B2
(45) Date of Patent: May 7, 2024

(54) MEDICAL SYSTEM AND METHOD OF USING THE SAME

(71) Applicant: TERUMO KABUSHIKI KAISHA, Tokyo (JP)

(72) Inventor: Kouta Hamuro, Fujinomiya (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 176 days.

(21) Appl. No.: 17/374,443

(22) Filed: Jul. 13, 2021

(65) Prior Publication Data

US 2021/0338246 A1    Nov. 4, 2021

Related U.S. Application Data

(62) Division of application No. 15/707,611, filed on Sep. 18, 2017, now Pat. No. 11,076,859.

(30) Foreign Application Priority Data

Sep. 27, 2016  (JP) .................................. 2016-187681

(51) Int. Cl.
*A61B 17/12* (2006.01)
*A61B 17/221* (2006.01)
(Continued)

(52) U.S. Cl.
CPC .. *A61B 17/12109* (2013.01); *A61B 17/12136* (2013.01); *A61B 17/221* (2013.01);
(Continued)

(58) Field of Classification Search
CPC ........ A61B 17/12109; A61B 17/12136; A61B 17/221; A61B 2017/2217; A61F 2/013; A61F 2/01; A61F 2/011; A61F 2/82; A61F 2/958; A61F 2002/016; A61F 2230/0071; A61F 2230/0091; A61F 2/0108;
(Continued)

(56) References Cited

U.S. PATENT DOCUMENTS 6,346,116 B1    2/2002  Brooks et al.
2003/0187495 A1*  10/2003  Cully ............... A61B 17/12109
                                                            623/1.34
(Continued)

FOREIGN PATENT DOCUMENTS

JP    2003506141 A    2/2003

*Primary Examiner* — Erich G Herbermann
*Assistant Examiner* — Aman Kumar Mann
(74) *Attorney, Agent, or Firm* — Buchanan Ingersoll & Rooney PC

(57) ABSTRACT

A method includes indwelling a filter inside a body lumen in a living body so that the filter is indwelled at a position downstream from a stenosed site in the body lumen, moving a collection device in a downstream direction within the living body from upstream of the stenosed site to the stenosed site while the filter remains indwelled at the position downstream from the stenosed site, engaging the filter with the collection device while the filter is indwelled at the position downstream from the stenosed site so that the filter is connected to the collection device, and removing the collection device and the filter from the living body by moving both the filter and the collection device in an upstream direction while the filter and the collection device are engaged with one another.

20 Claims, 10 Drawing Sheets

(51) Int. Cl.
*A61F 2/01* (2006.01)
*A61F 2/82* (2013.01)
*A61F 2/958* (2013.01)
*A61M 25/09* (2006.01)

(52) U.S. Cl.
CPC .............. *A61F 2/01* (2013.01); *A61F 2/013* (2013.01); *A61B 2017/2217* (2013.01); *A61F 2/011* (2020.05); *A61F 2002/016* (2013.01); *A61F 2/82* (2013.01); *A61F 2/958* (2013.01); *A61F 2230/0071* (2013.01); *A61F 2230/0091* (2013.01); *A61M 2025/09175* (2013.01)

(58) Field of Classification Search
CPC .... A61F 2002/9528; A61F 2220/0016; A61M 2025/09175
See application file for complete search history.

(56) References Cited

U.S. PATENT DOCUMENTS

| | | |
|---|---|---|
| 2004/0006370 A1 | 1/2004 | Tsugita |
| 2005/0267512 A1* | 12/2005 | Osborne ............... A61F 2/0103 606/200 |
| 2008/0208245 A1* | 8/2008 | Hoffman ............... A61F 2/0108 606/200 |
| 2009/0163926 A1 | 6/2009 | Sos |
| 2012/0005876 A1 | 1/2012 | Bregulla |
| 2012/0035647 A1* | 2/2012 | Bregulla ............... A61F 2/0105 606/200 |
| 2012/0130418 A1 | 5/2012 | Jenson et al. |
| 2013/0041391 A1 | 2/2013 | Spencer et al. |
| 2014/0243878 A1 | 8/2014 | Urbanski et al. |
| 2018/0085129 A1 | 3/2018 | Hamuro |

* cited by examiner

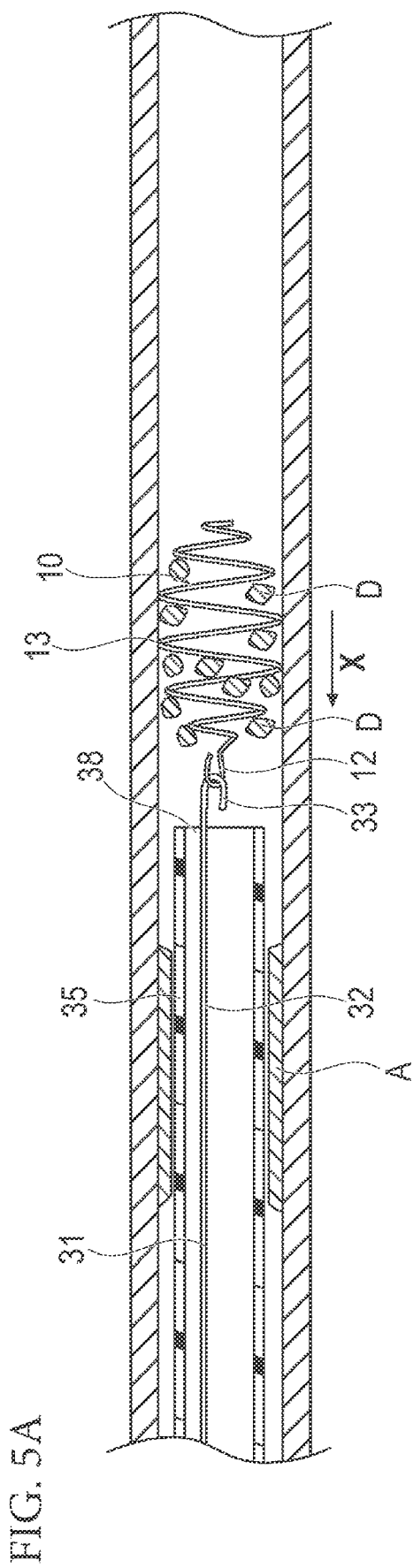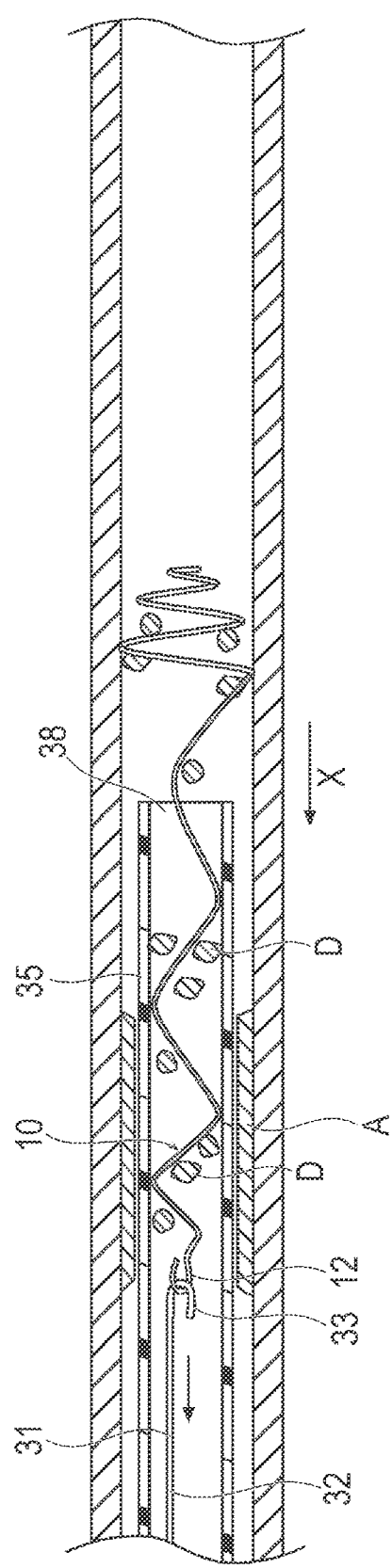

MEDICAL SYSTEM AND METHOD OF USING THE SAME

CROSS-REFERENCES TO RELATED APPLICATIONS

This application is a divisional application of U.S. patent application Ser. No. 15/707,611 filed Sep. 18, 2017, and claims priority to Japanese Application No. 2016-187681 filed on Sep. 27, 2016, the entire content of both of which is incorporated herein by reference.

TECHNICAL FIELD

The present invention generally relates to a medical system used for removing an object from a body lumen and a method of using a medical system.

BACKGROUND DISCUSSION

There is a known method of treating a lesion area having occlusion or stenosis of a body lumen (such as a blood vessel) that uses a device (a balloon catheter or a stent indwelling catheter), which is percutaneously insertable into a body lumen. There is a possibility that a large amount of thrombus separates and falls from a lesion area and flows to the downstream side as debris during treatment performed using the balloon catheter. For example, debris may be easily generated because the amount of thrombus is large in the case of a lesion area of a lower extremity artery. It is not desirable that the debris flows along with blood because a distal blood vessel may be blocked.

For this reason, there is known a method of indwelling a filter at the downstream side of the thrombus before the treatment using the balloon catheter. For example, Japanese Patent Application Publication No. 2003-506141 describes a method of indwelling a filter. When the lesion area is a chronic total occlusion (CTO), there is a need to break a part of the occluded portion at the time of indwelling the filter from the upstream side of the lower extremity artery. Since the debris is generated before the indwelling of the filter, the debris is undesirably not completely trapped (i.e., captured). Thus, there is also known a method of introducing the filter from the downstream side (the distal side) of the lower extremity artery so that the filter does not to pass through the lesion area. When the filter is introduced from the downstream side of the lower extremity artery, the filter can be indwelled so that the filter cannot pass through the lesion area and thus the debris can be effectively trapped.

SUMMARY

The blood vessel at the downstream side (i.e., the distal side) of the lower extremity artery is thinner than the blood vessel at the upstream side (i.e., proximal to the blood vessel at the distal side). It is thus difficult to collect a large amount of debris trapped by the filter from the downstream side when the filter is introduced from the downstream side of the lower extremity artery.

The medical system and method disclosed here are capable of effectively trapping an object inside a body lumen and removing the object to the outside of a body.

A method includes indwelling a filter inside a body lumen in a living body so that the filter is indwelled at a position downstream from a stenosed site in the body lumen, moving a collection device in a downstream direction within the living body from upstream of the stenosed site to the stenosed site while the filter remains indwelled at the position downstream from the stenosed site, engaging the filter with the collection device while the filter is indwelled at the position downstream from the stenosed site so that the filter is connected to the collection device, and removing the collection device and the filter from the living body by moving both the filter and the collection device in an upstream direction while the filter and the collection device are engaged with one another.

The filter can be collected while being pulled in the first direction (e.g., in the upstream direction or proximally relative to the collection device or distally relative to the filter) after the second engagement portion engages with the first engagement portion from the first direction side. At this time, the first engagement portion is positioned at the first direction side of the trapping portion. The second engagement portion of the collection shaft can thus easily engage with the first engagement portion from the first direction side and can pull the trapping portion in the first direction (e.g., in the upstream direction or proximally relative to the collection device or distally relative to the trapping portion).

The method involves indwelling the filter (trapping device) at the downstream side of the lesion area by inserting a conveying device into the body lumen from the downstream side of the lesion area so as not to pass through the lesion area. For this reason, it is possible to effectively trap any object(s) separated from the lesion area. After the treatment for the lesion area is completed, the collection device is inserted into the body lumen from the upstream side of the lesion area. An engagement portion of the collection device engages the filter, and the filter is pulled in the upstream direction to be collected by the collection device. At this time, the filter is positioned so the engagement portion of the collection device can relatively easily engage the filter and can be relatively easily pulled in the upstream direction. The method thus helps make it possible to effectively collect the object(s) trapped by the filter along with the filter itself by using the body lumen at the upstream side of the lesion area.

The collection device may further include a collection pipe body which is able to accommodate the collection shaft and to collect the trapping portion from a distal opening portion into the collection pipe body. The collection shaft may protrude from the distal opening portion of the collection pipe body to engage with the trapping portion and may be able to pull the trapping portion into the collection pipe body. Accordingly, the object trapped by the trapping portion can be effectively collected by the collection pipe body along with the trapping portion since the trapping portion is pulled by the collection shaft.

In the trapping portion, a collection assisting portion which extends inward in a radial direction of the trapping portion while extending toward the first direction may be provided in an outer peripheral surface extending toward the first direction from a maximum portion having a maximum outer diameter in an expanded state. Accordingly, when the trapping portion that has been expanded and indwelled in the body lumen is then pulled in the first direction (toward the proximal end of the elongated shaft of the collection device), the collection assisting portion smoothly contacts a body tissue or the collection pipe body. The trapping portion can thus be easily collected and a damage of the body tissue can be prevented.

The trapping portion may be contracted inward in the radial direction of the trapping portion when a force is applied to the first engagement portion in the first direction. Accordingly, since the trapping portion is contracted when the trapping portion is pulled in the first direction, the trapping portion can be easily collected.

The trapping portion may be contracted inward in the radial direction of the trapping portion when a twisting force is applied to the first engagement portion. Accordingly, since the trapping portion is contracted when the twisting force is applied to the first engagement portion of the trapping portion, the trapping portion can be easily collected.

According to another aspect, a method comprises: moving a tubular body inside a body lumen in a living body so that the distal end of the tubular body approaches a stenosed site in the body lumen from a position downstream of the stenosed sit; moving a filter positioned inside the tubular body to a position outside the tubular body, with the moving of the filter to the position outside the tubular body occurring while the distal end of the tubular body is positioned downstream of the stenosed site; moving a hollow tube inside the body lumen in the living body toward the stenosed site from a position upstream of the stenosed site; positioning the filter in a lumen in the hollow tube; and removing the hollow tube and the filter from the living body while the filter is positioned in the lumen in the hollow tube by moving both the filter and the hollow tube in an upstream direction.

In yet another aspect of the disclosure, a method involves positioning a filter in a body lumen in a living body so that the filter is positioned downstream from a stenosis in the body lumen, treating the stenosis while the filter remains positioned downstream from the stenosis to create an enlarged a-passage through the stenosis, trapping debris resulting from the treating of the stenosis in the filter, moving the filter that is positioned downstream from the stenosis in an upstream direction so that the filter passes through the passage in the stenosis after the treating of the stenosis, with the moving of the filter in the upstream direction including moving the debris trapped in the filter, and removing the filter and the debris trapped in the filter from the living body after the filter passes through the passage in the stenosis.

BRIEF DESCRIPTION OF THE DRAWINGS

FIG. 3A illustrates a conveying device being inserted into a blood vessel and FIG. 3B illustrates a trapping portion indwelling in a blood vessel.

FIG. 4A illustrates a balloon catheter being inserted into a blood vessel, and FIG. 4B illustrates the balloon in the expanded state.

FIGS. 5A and 5B are cross-sectional views illustrating the interior state of blood vessel. FIG. 5A illustrates a collection device being inserted into a blood vessel, and FIG. 5B illustrates the trapping portion being collected by the collection device.

FIG. 8A illustrates a second modified example, and FIG. 8B illustrates a third modified example.

FIG. 9A illustrates a state before a collection shaft engages with a trapping portion, and FIG. 9B illustrates a state where the collection shaft engages with the trapping portion.

FIG. 10A illustrates a state before a collection shaft engages with a trapping portion, and FIG. 10B illustrates a state where the collection shaft engages with the trapping portion.

FIG. 11A illustrates a state where a collection shaft engages with a trapping portion, and FIG. 11B illustrates a state where the trapping portion is pulled by the collection shaft.

FIG. 12A illustrates a state where a collection shaft engages with a trapping portion, and FIG. 12B illustrates a state where the trapping portion is pulled by the collection shaft.

FIG. 13A illustrates an eighth modified example, and FIG. 13B illustrates a ninth modified example.

FIG. 14A illustrates a state where a collection shaft engages a trapping portion, and FIG. 14B illustrates a state where the trapping portion is pulled by the collection shaft.

FIG. 15A illustrates an eleventh modified example, and FIG. 15B illustrates a twelfth modified example.

DETAILED DESCRIPTION

Figure 1:
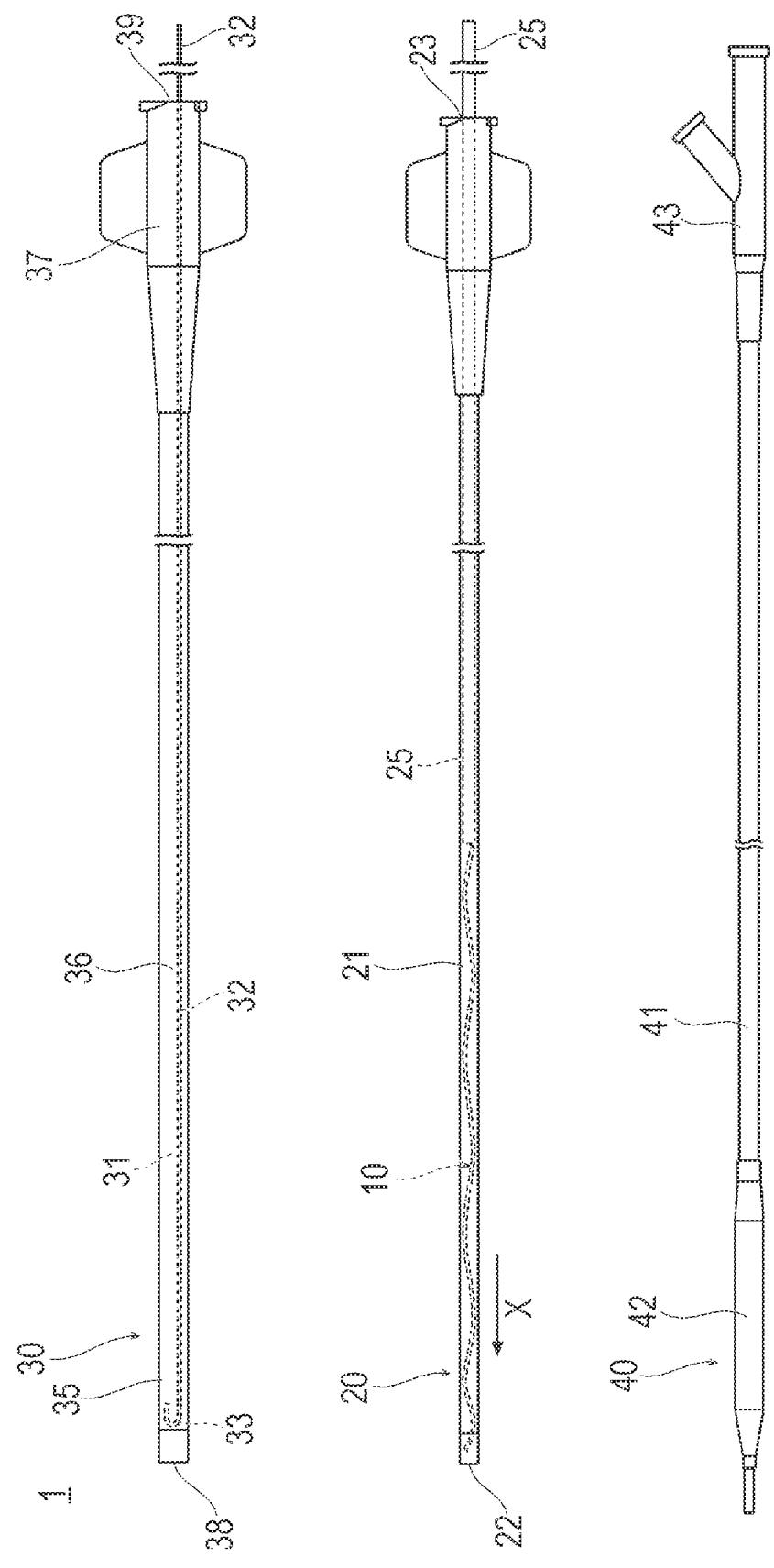
FIG. 1 is a top view illustrating a medical system according to an embodiment.

Set forth below with reference to the accompanying drawings is a detailed description of embodiments of a medical system and method using a medical system representing examples of the inventive medical system and method disclosed here. It should be noted that the dimensional ratios in the drawings may be exaggerated and may be different from the actual ratios for convenience of description or illustration.

A medical system 1 according to an embodiment is a device which traps debris (i.e., one or more objects or pieces) generated by separated thrombus, plaque, calcified lesion, and the like of a lesion area. The device is configured to remove the debris to the outside of a living body (i.e., to move the debris from inside the living body to outside the living body) at the time of treating a lesion area having occlusion or stenosis of a lower extremity artery. The side of the device that is configured to be inserted into the blood vessel will be referred to as a "distal side", "distal portion" or "distal end." The side of the device that is configured to be operated (e.g., by an operator or user) will be referred to as a "proximal side", "proximal portion" or "proximal end". The object(s) to be removed is not necessarily limited to thrombus, plaque, and calcified lesion. All objects that may exist in a body lumen may be applicable. The source side of the blood flow in the blood vessel will be referred to as an "upstream side" and the side on which blood flow goes will be referred to as a "downstream side". In the artery, the downstream side is the distal side.

Figure 2:
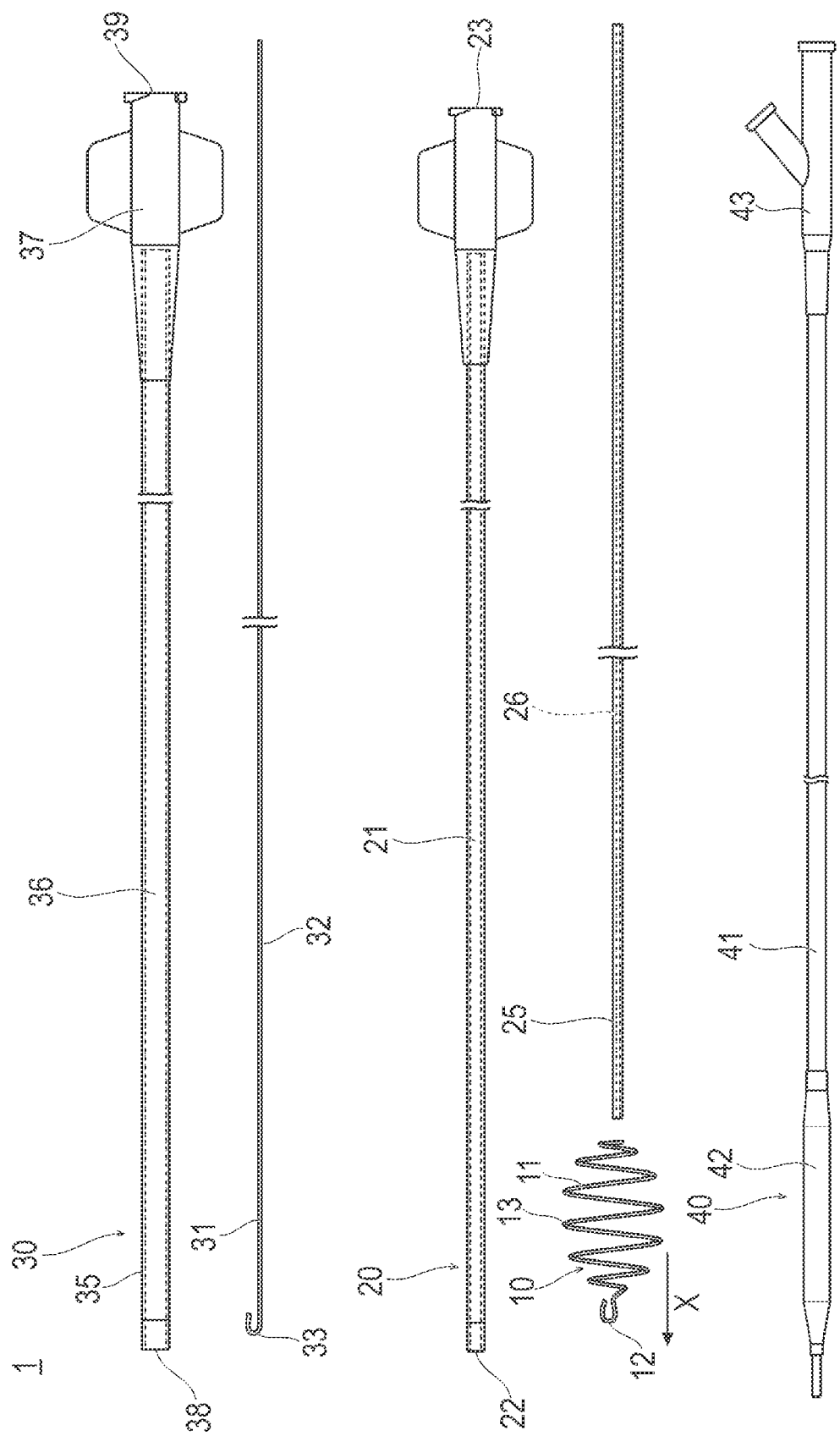
FIG. 2 is a top view illustrating a state where components of the medical system according to the embodiment are divided.

The medical system 1 according to the embodiment illustrated in FIGS. 1 and 2 includes a trapping portion 10, a conveying device 20, a collection device 30, and a treatment device 40.

The trapping portion 10 serves as a filter (i.e., a collector) which traps debris inside a blood vessel. The trapping portion 10 is a spiral wire material which can be elastically expanded and contracted (i.e., the trapping portion 10 is expandable and contractible, or the trapping portion 10 is configured to expand and contract). In a natural state where no external force is exerted, the trapping portion 10 expands (e.g., radially outward) by an elastic force (a restoring force) of the trapping portion 10 (see FIG. 2). The trapping portion 10 includes a spiral portion 11 which is formed in a spiral shape (i.e., spiral-shaped) when the trapping portion 10 is in an expanded state. The trapping portion 10 includes a first engagement portion 12 at the first direction X side of the spiral portion 11 (e.g., the first engagement portion 12 is at the distal end of the spiral portion 11 as shown in FIG. 2). When the trapping portion 10 is disposed inside the blood vessel, the trapping portion 10 is inserted into the blood vessel from the first engagement portion 12 side so that the first engagement portion 12 is positioned at the upstream side. The first direction X is the upstream direction. The first direction X is also the direction that the first engagement portion 12 of the trapping portion 10 faces (i.e., the first engagement portion 12 moves distally or upstream in the first direction X when being inserted into the body lumen), and is the direction that the trapping portion 10 is collected by the collection device 30 inside the blood vessel (i.e., the collection device 30 moves in the first direction X to remove the trapping portion 10 from the living body). The spiral portion 11 includes a maximum portion 13 which has the largest outer diameter relative to the remainder of the spiral portion 11. The maximum portion 13 is formed substantially at the center of a direction following a spiral center axis. A portion of the spiral portion 11 on the first direction X side in relation to the maximum portion 13 gradually decreases in outer diameter toward the first engagement portion 12 (i.e., toward the distal end of the spiral portion 11). Another portion of the spiral portion 11 gradually decreases in outer diameter from the maximum portion 13 in a direction opposite to the first direction X (i.e., toward the proximal end of the spiral portion 11).

The first engagement portion 12 is able to (i.e., configured to) engage with a second engagement portion 33 provided in the collection device 30. The engagement indicates an engagement in which two portions (i.e., the first engagement portion 12 and the second engagement portion 33) contact each other and one portion moves while the other portion also moves (i.e., move together in conjunction with one another). The first engagement portion 12 is a hook which is formed by bending an end of a wire forming the trapping portion 10.

A length along the spiral center axis (i.e., in the axial or longitudinal direction through the center of the wound spiral from the proximal end of the trapping portion to the distal end of the trapping portion) of the trapping portion 10 in an expanded state can be appropriately changed and is, for example, 5 to 50 mm. An outer diameter of the maximum portion 13 in an expanded state can be appropriately changed in response to an inner diameter of the blood vessel that the trapping portion 10 is deployed with. For example, the outer diameter of the maximum portion 13 of the trapping portion 10 when the trapping portion 10 is in the expanded state is 3 to 15 mm. An outer diameter of a wire forming the trapping portion 10 can be appropriately set (selected) and is, for example, 0.1 to 2 mm.

The trapping portion 10 material is desirably a flexible material. For example, the trapping portion 10 material may be a metal material such as a shape memory alloy which has a shape memory effect or superelasticity by a heat treatment, stainless steel, tantalum (Ta), titanium (Ti), platinum (Pt), gold (Au), and tungsten (W), a resin material such as polyolefin like polyethylene and polypropylene, polyamide, polyester like polyethylene terephthalate, fluorine-based polymer like ETFE (tetrafluoroethylene·ethylene copolymer), PEEK (polyether ether ketone), and polyimide, or a combination of the metal material and the resin material can be appropriately used. As the shape memory alloy, Ni—Ti type, Cu—Al—Ni type, and Cu—Zn—Al type or a combination of these materials is preferably used. As a structure obtained by combining a plurality of materials, for example, a structure in which a core wire formed of Pt is coated with a Ni—Ti alloy for a contrasting property or a structure in which a core wire formed of a Ni—Ti alloy is plated with gold can be exemplified.

The conveying device 20 is a device which conveys the trapping portion 10 into the blood vessel. The conveying device 20 includes a conveying pipe body 21 (hollow tube) which is able to accommodate the trapping portion 10 (i.e., the trapping portion 10 may be housed within the interior of the conveying pipe body 21) and a pressing shaft 25 which discharges the trapping portion 10 from the conveying pipe body 21.

The conveying pipe body 21 includes a distal opening portion 22 which is provided at the distal end and a proximal opening portion 23 which is provided at the proximal end. The conveying pipe body 21 can accommodate the contracted trapping portion 10 and the pressing shaft 25 within the interior of the conveying pipe body 21. The conveying pipe body 21 can accommodate the trapping portion 10 inside the distal portion of the conveying pipe body 21 and can accommodate the pressing shaft 25 at the proximal side of the trapping portion 10. The first direction X of the trapping portion 10 faces the distal side of the conveying pipe body 21. The proximal portion of the pressing shaft 25 when the pressing shaft 25 is inserted within the conveying pipe body 21 protrudes toward the proximal side in relation to the proximal opening portion 23 so that an operator may operate (move) the pressing shaft 25 in the axial direction.

The pressing shaft 25 is an elongated pipe (tubular or cylindrical) body which can be accommodated inside the conveying pipe body 21. The pressing shaft 25 includes a through-hole 26 into which a guide wire is insertable (i.e., a guide wire may be inserted through the through-hole 26 of the pressing shaft 25). In some embodiments, the pressing shaft 25 may not include the through-hole 26. When the pressing shaft 25 moves toward the distal side (distally) relative to the conveying pipe body 21, the trapping portion 10 inside the conveying pipe body 21 can be discharged from the distal opening portion 22.

The conveying pipe body 21 material is not particularly limited. For example, polyolefin such as polyethylene, polypropylene, ethylene-propylene copolymer, and ethylene-vinyl acetate copolymer, polyvinyl chloride, polystyrene, polyamide, polyimide, or a combination thereof can be suitably used as the material forming the conveying pipe body 21. The conveying pipe body 21 may be formed of a plurality of materials and may have a reinforcement member such as a wire embedded therein.

The pressing shaft 25 material is not particularly limited, and a material which is applicable to the conveying pipe body 21 or the trapping portion 10 can be used.

The collection device 30 is a device which collects the trapping portion 10 that has been indwelled inside the blood vessel. The collection device 30 includes a collection shaft 31 and a guiding catheter 35 (a collection pipe body).

The collection shaft 31 includes a shaft base portion 32 which extends linearly (i.e., in the axial direction) and the second engagement portion 33 which is provided at the distal side (distal end) of the shaft base portion 32. The second engagement portion 33 can engage with the first engagement portion 12 of the trapping portion 10. The second engagement portion 33 is a hook which is formed by bending an end of a wire forming the collection shaft 31.

The collection shaft 31 material is not particularly limited. For example, stainless steel, a shape memory alloy, or the like can be preferably used to form the collection shaft 31.

The guiding catheter 35 is a known catheter which is generally used. The guiding catheter 35 includes a catheter pipe body 36 and a catheter hub 37. The catheter pipe body 36 includes a lumen which can accommodate the collection shaft 31 and the trapping portion 10 therein (i.e., within the lumen of the catheter pipe body 36). The distal end of the catheter pipe body 36 includes a distal opening portion 38. The catheter hub 37 is fixed to the proximal end of the catheter pipe body 36. The catheter hub 37 includes a proximal opening portion 39 which communicates with the distal opening portion 38.

The catheter pipe body 36 material is not particularly limited and, for example, polyolefin such as polyethylene, polypropylene, ethylene-propylene copolymer, and ethylene-vinyl acetate copolymer, polyvinyl chloride, polystyrene, polyamide, polyimide or a combination thereof can be suitably used as the material forming the catheter pipe body 36. The catheter pipe body 36 may be formed of a plurality of materials and may have a reinforcement member such as a wire embedded therein.

The treatment device 40 is a known balloon catheter 40 which is generally used. The balloon catheter 40 includes an elongated shaft portion 41, a balloon 42 provided at the distal portion of the shaft portion 41, and a balloon catheter hub 43 fixed to the proximal end of the shaft portion 41. The balloon 42 expands or contracts (i.e., radially outwardly or inwardly) by supplying or discharging a fluid from the balloon catheter hub 43. Additionally, the treatment device may not be the balloon catheter. The treatment device may be any device used in treatment in which debris is possibly generated from the lesion area. For example, the treatment device may be a device which indwells a stent, or an atherectomy device which cuts thrombus, and the like.

Next, a method of using the medical system 1 illustrated in FIGS. 1 and 2 will be described by an example case in which a lesion area A (see FIG. 3A) having occlusion or stenosis of a lower extremity is treated. The conveying device 20 is inserted from a downstream side (a distal side) in relation to the lesion area A into the blood vessel. The artery into which the conveying device 20 is inserted is, for example, a common femoral artery, a superficial femoral artery, a popliteal artery, an anterior tibial artery, a posterior tibial artery, a lumbar artery, a plantar artery, or a dorsalis artery. The collection device 30 is positioned at an artery at the upstream side of the lesion area A. The artery into which the collection device 30 is inserted is, for example, a radial artery or a brachial artery. The artery at the upstream side of the lower extremity artery is generally thicker than the downstream artery.

First, an introducer sheath (not illustrated) is percutaneously inserted into the blood vessel at the downstream side of the lesion area A. Next, the guide wire 50 is inserted into the blood vessel through the introducer sheath.

Next, the conveying device 20 is prepared so that the trapping portion 10 and the pressing shaft 25 are accommodated inside the conveying pipe body 21 as illustrated in FIG. 1. The trapping portion 10 is disposed at a position close to the distal end of the conveying pipe body 21 and is constrained in a contracted state (i.e., the inner wall of the conveying pipe body 21 prevents the trapping portion 10 from expanding radially outward to hold the trapping portion 10 in the contracted state). The pressing shaft 25 protrudes from the proximal opening portion 23 toward the proximal side (i.e., the proximal end of the pressing shaft 25 is proximal to the proximal opening portion 23).

Figure 3A:
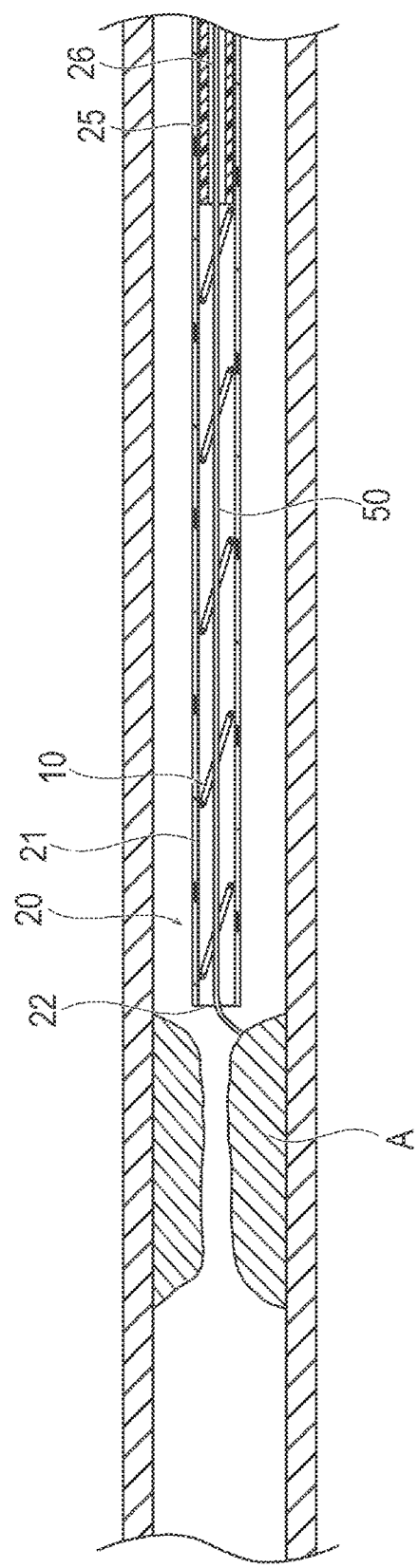
FIGS. 3A and 3B are cross-sectional views illustrating the interior state of a blood vessel.

The proximal end of the guide wire 50, which is located outside of the living body, is inserted into the through-hole 26 of the lumen and the pressing shaft 25 of the conveying pipe body 21. Subsequently, the conveying pipe body 21 is advanced along the guide wire 50 to reach the downstream side of the lesion area A as shown in FIG. 3A.

Figure 3B:
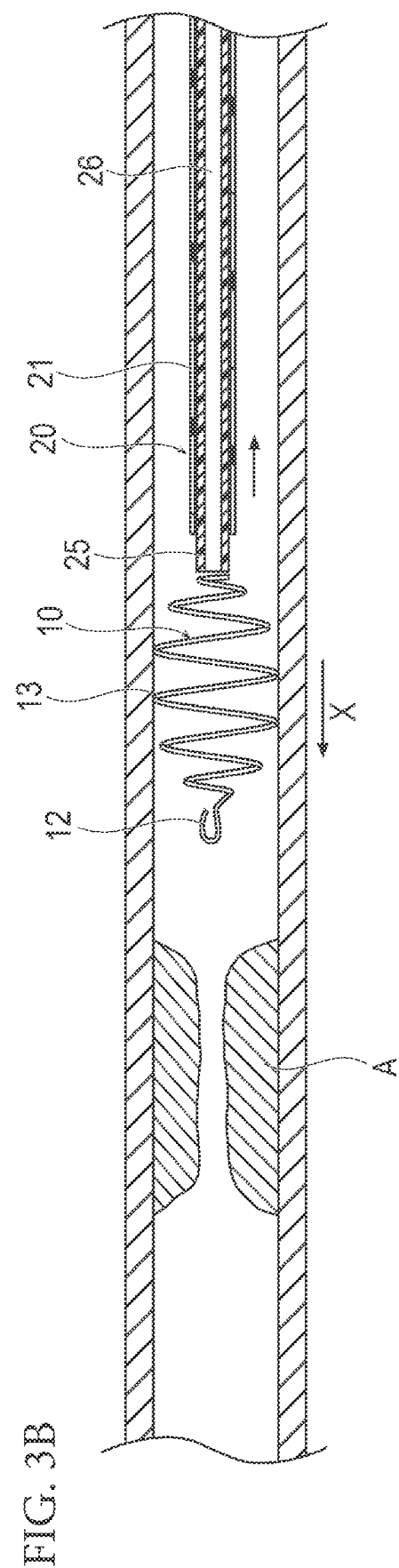

Next, the conveying pipe body 21 is moved to the proximal side (proximally, e.g., by the operator) while the movement of the pressing shaft 25 is restricted by an operator's hand (e.g., the operator holds the pressing shaft 25 in place so that the conveying pipe body 21 moves proximally relative to the pressing shaft 25). Alternatively, the pressing shaft 25 may be moved to the distal side (distally, e.g., by the operator) while the movement of the conveying pipe body 21 is held by an operator's hand. At some time (or the entire time) during this relative movement between the conveying pipe body 21 and the pressing shaft 25, the distal end of the pressing shaft 25 contacts the trapping portion 10. Then, when the conveying pipe body 21 moves to the proximal side (proximally) relative to the pressing shaft 25, the trapping portion 10 is discharged from the distal opening portion 22 of the conveying pipe body 21 as illustrated in FIG. 3B. The trapping portion 10 then expands radially outwardly by a self-restoring force. A range (a portion) of the trapping portion 10 including the maximum portion 13 contacts the inner wall surface of the blood vessel. The expandable maximum diameter of the trapping portion 10 is larger than the inner diameter of the blood vessel into which the trapping portion 10 is inserted. For this reason, the trapping portion 10 is bitten into the blood vessel (i.e., the trapping portion 10 embeds into the inner wall of the blood vessel) while enlarging the blood vessel so that the trapping portion 10 is strongly indwelled to/in the blood vessel. The trapping portion 10 is eventually discharged (removed) from a portion on the first direction X side. Thus, the first engagement portion 12 is directed toward the upstream side inside the blood vessel. The trapping portion 10, which is indwelled at the downstream side of the lesion area A, serves as a filter which traps any debris D (see FIG. 4B) generated from the lesion area A without disturbing the blood flow.

Next, the guide wire 50, the conveying pipe body 21, and the pressing shaft 25 are removed to the outside of the body (i.e., removed from the living body). An operation of indwelling the trapping portion 10 using the conveying device 20 is thus completed. At the time of indwelling the trapping portion 10, the conveying device 20 is inserted from the downstream side of the lesion area A and the trapping portion 10 is indwelled at the downstream side of the lesion area A (i.e., the trapping portion 10 indwells at a position downstream from the lesion area A). The conveying device 20 thus does not need to pass through the lesion area A. The trapping portion 10 can thereby be easily indwelled. Further, safety (i.e., to the patient) is relatively high since the debris D is not generated from the lesion area A when indwelling the trapping portion 10. Additionally, the distal blood vessel of the lower extremity artery is thin, but an operation of conveying and indwelling the trapping portion 10 can be performed without any problem (i.e., relatively easily).

Next, an introducer sheath (not illustrated) is percutaneously inserted into the blood vessel at the upstream side of the lesion area A. A guide wire 51 is then inserted into the blood vessel through this introducer sheath.

The proximal end of the guide wire 51, which is positioned outside of the living body, is inserted into the distal opening portion 38 of the guiding catheter 35. Subsequently, the guiding catheter 35 is advanced (moved distally) along the guide wire 51 to reach the upstream side of the lesion area A.

Figure 4A:
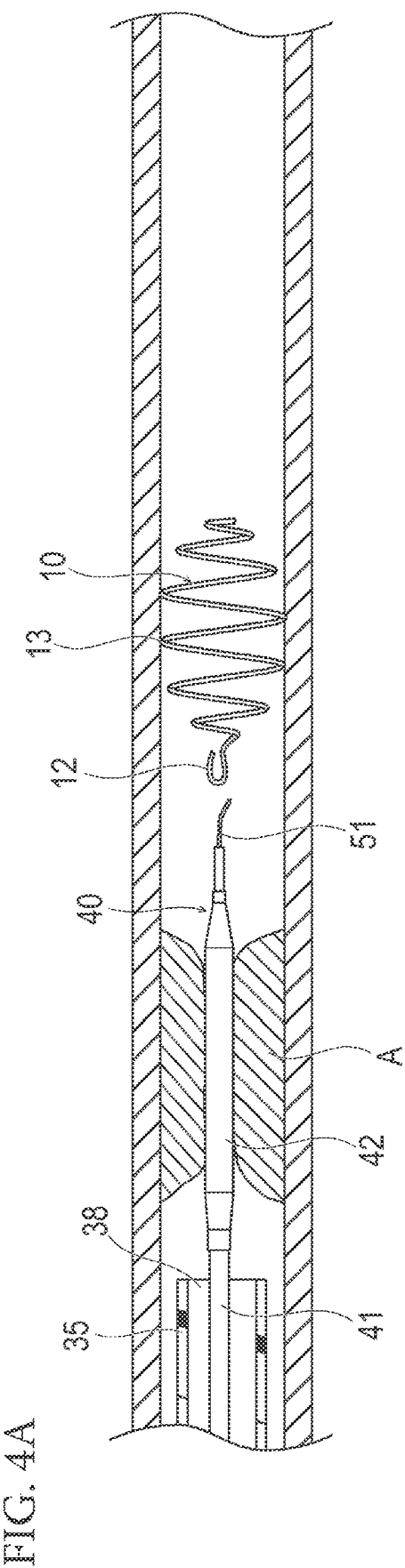
FIGS. 4A and 4B are cross-sectional views illustrating the interior state of a blood vessel.

The proximal end of the guide wire 51, which is positioned outside of the living body, is then inserted into the lumen of the balloon catheter 40. Subsequently, as illustrated in FIG. 4A, the balloon catheter 40 is advanced along the guide wire 51 to reach the lesion area A. A separately prepared support catheter can be used so that the guide wire 51 passes through the lesion area A. When the guide wire 51 and the balloon catheter 40 are positioned inside the lesion area A, there is a possibility that a thrombus is separated from the lesion area A so that the debris D is generated. Since the trapping portion 10 is already indwelled at the downstream side of the lesion area A, however, the debris D is trapped by the trapping portion 10. For this reason, safety is high because it is possible to suppress the debris D from flowing to a distal blood vessel.

Figure 4B:
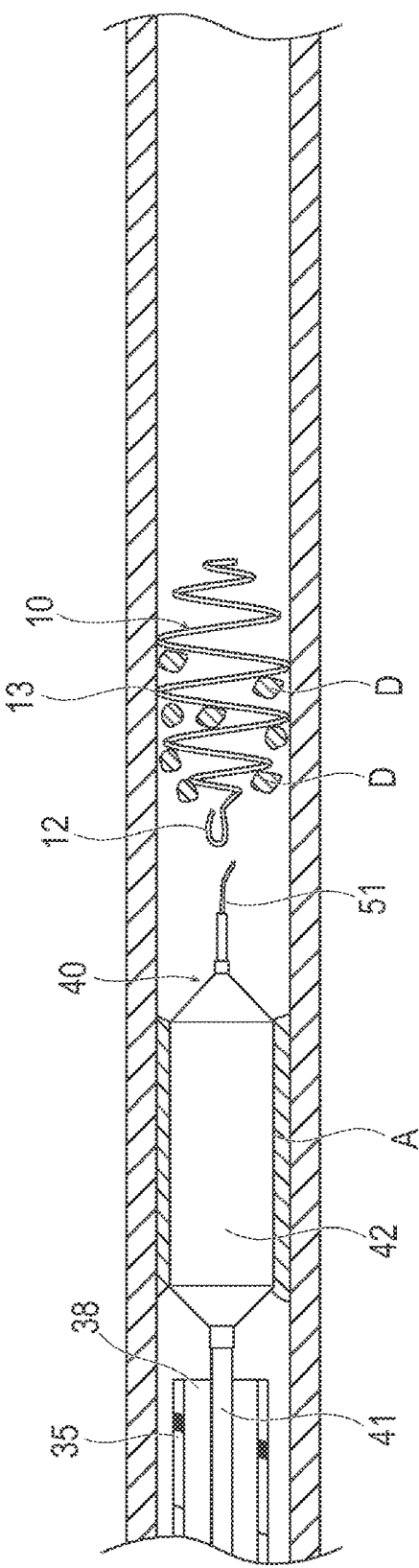

Next, a fluid is supplied from the balloon catheter hub 43 to the interior of the balloon 42 to expand the balloon 42 radially outwardly (i.e., inflate the balloon 42) as illustrated in FIG. 4B. Accordingly, the lesion area A is widened by the balloon 42 to help ensure a blood flow path exists. Subsequently, the fluid of the balloon 42 is discharged from the balloon catheter hub 43 to contract the balloon 42 radially inwardly (i.e., deflate the balloon 42). The guiding catheter 35 is left inside the blood vessel and the balloon catheter 40 is removed to the outside of the body (i.e., from the living body). The treatment using the balloon catheter 40 is thus completed. When performing treatment using the balloon catheter 40, there is a possibility that the thrombus is separated from the lesion area A (widened by the balloon 42), so that the debris D is generated. However, since the trapping portion 10 is indwelled at the downstream side of the lesion area A, the debris D is trapped by the trapping portion 10. Since it is possible to suppress the debris D from flowing to the distal blood vessel, safety is relatively high.

Next, the guiding catheter 35 is pushed (distally or in the downstream direction) to the vicinity of the trapping portion 10. When the guiding catheter 35 is moved distally in this manner, there is a possibility that the thrombus is separated from the lesion area A and the debris D is generated. The debris D, however, becomes trapped by the trapping portion 10. Next, the distal end (provided with the second engagement portion 33) of the collection shaft 31 is inserted into the catheter hub 37 of the guiding catheter 35. Subsequently, the collection shaft 31 is pushed forward (distally) so that the second engagement portion 33 protrudes from (i.e., distally beyond) the distal opening portion 38 of the guiding catheter 35 into the blood vessel as illustrated in FIG. 5A. In some embodiments, the second engagement portion 33 may not protrude from the guiding catheter 35 as long as the second engagement portion can engage with the first engagement portion 12. Subsequently, the second engagement portion 33 engages (i.e., axially overlaps to contact and join together) with the first engagement portion 12. At this time, since the first engagement portion 12 is positioned at the upstream side (the first direction X side) of the trapping portion 10, the first engagement portion can easily engage with the second engagement portion 33 (which is inserted from the upstream side).

Figure 6:
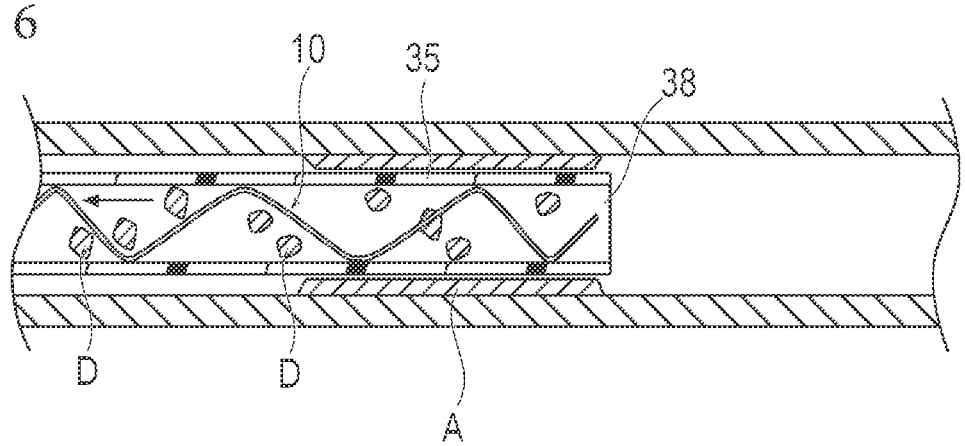
FIG. 6 is a cross-sectional view illustrating the trapping portion being collected by the collection device.

Next, the collection shaft 31 is moved toward the upstream side in the guiding catheter 35. The trapping portion 10 thus moves in the upstream direction (the first direction X) to contact the guiding catheter 35. The trapping portion 10 which contacts the guiding catheter 35 is contracted radially inward into a size (i.e., sufficiently small in outer diameter) to be accommodated into the guiding catheter 35. The trapping portion 10 is thereby accommodated inside the guiding catheter 35 as illustrated in FIG. 5B. Subsequently, the entirety of the trapping portion 10 is accommodated in the guiding catheter 35 as illustrated in FIG. 6. The debris D which has been trapped by the trapping portion 10 is also accommodated in the guiding catheter 35 along with the trapping portion 10. The inner diameter of the guiding catheter 35 inserted at the upstream side of the lower extremity artery is larger than the inner diameter of the conveying pipe body 21 inserted at the downstream side. For this reason, it is possible to effectively accommodate the trapping portion inside the guiding catheter 35 even when a relatively large amount of the debris D is generated. The operation of collecting the trapping portion 10 and removing the guiding catheter 35 accommodating the debris D to the outside of the body (i.e., from the living body) along with the trapping portion 10 is thus completed.

As described above, the medical system 1 according to the embodiment is the medical system 1 which traps an object inside the body lumen, including: the trapping portion 10 which is able to be elastically expanded and contracted, the conveying device 20 which is able to accommodate the elastically contracted trapping portion 10 and to discharge the trapping portion 10 to the outside while expanding the trapping portion; and the collection device 30 which is able to collect the trapping portion 10 while contracting the trapping portion, the trapping portion 10 includes the first engagement portion 12 formed at the first direction X side, the conveying device 20 is able to discharge the trapping portion 10 to the outside while the first direction X side is directed to the distal side of the conveying device 20, the collection device 30 includes the elongated collection shaft 31 having the second engagement portion 33 engaging with the first engagement portion 12, and the second engagement portion 33 is able to pull the first engagement portion 12 engaging with the second engagement portion 33 in the first direction X.

The medical system 1 with the above-described configuration can indwell the trapping portion 10 at the downstream side of the lesion area A without passing through the lesion area A by inserting the conveying device 20 into the body lumen from the downstream side of the lesion area A. It is thus possible to effectively trap the debris D separated from the lesion area A. Further, after the treatment of the lesion area A is completed, the collection device 30 is inserted into the body lumen from the upstream side of the lesion area A to collect (retrieve) the trapping portion 10. At this time, the first engagement portion 12 is positioned at the first direction X side, that is, the upstream side of the trapping portion 10. The second engagement portion 33 of the collection shaft 31 can thereby easily engage with the first engagement portion 12 from the upstream side. The first engagement portion 12 engaging with the second engagement portion 33 can be pulled to the upstream side to be collected. Thus, it is possible to effectively collect the debris D trapped by the trapping portion 10 along with the trapping portion 10 by using the (relatively) thick blood vessel at the upstream side of the lesion area A. This medical system 1 is particularly effective when the lesion area A is totally occluded since the conveying device 20 does not pass through the lesion area A when the trapping portion 10 is indwelled.

The collection device 30 includes the guiding catheter 35 (the collection pipe body) which is able to accommodate the collection shaft 31 and to collect the trapping portion 10 into the guiding catheter 35 from the distal opening portion 38. The collection shaft 31 protrudes from the distal opening portion 38 of the guiding catheter 35 and engages with the trapping portion 10 so that the trapping portion 10 can be pulled into the guiding catheter 35. Accordingly, the debris D trapped by the trapping portion 10 can be effectively collected to the guiding catheter 35 along with the trapping portion 10 when the trapping portion 10 is pulled by the collection shaft 31.

A method of using the medical system 1 includes steps of discharging the trapping portion 10 from the conveying device 20, accommodating the trapping portion 10 in an elastically contracted state and expanding the trapping portion 10, engaging the second engagement portion 33 with the first engagement portion 12 from the first direction X side, and pulling the trapping portion 10 in the first direction X by the collection shaft 31.

In the method of using the medical system 1, the second engagement portion 33 engages with the first engagement portion 12 from the first direction X side and the trapping portion 10 can be collected while being pulled in the first direction X. At this time, the first engagement portion 12 is positioned at the first direction X side of the trapping portion 10. For this reason, the second engagement portion 33 of the collection shaft 31 can easily engage with the first engagement portion 12 from the first direction X side and the trapping portion 10 can be pulled in the first direction X.

This disclosure also relates to a treatment method (a curing method) using the above-described medical system 1. The treatment method includes steps of inserting the conveying device 20 accommodating the trapping portion 10 in an elastically contracted state from the downstream side of the lesion area A into the body lumen and introducing the conveying device 20 to the downstream position of the lesion area A, discharging the trapping portion 10 from the conveying device 20 in an expanded state and indwelling the trapping portion in the body lumen, trapping the debris D separated from the lesion area A by the trapping portion 10, inserting the collection device 30 into the body lumen from the upstream side of the lesion area A, engaging the second engagement portion 33 with the first engagement portion 12, and pulling the collection shaft 31 in the upstream direction (the first direction X) and accommodating the trapping portion 10 in the collection device 30 along with the debris D trapped by the trapping portion.

In this treatment method, the conveying device 20 can be inserted into the body lumen from the downstream side of the lesion area A and the trapping portion 10 can be indwelled at the downstream side of the lesion area A so as not to pass through the lesion area A. The treatment method may make it possible to effectively trap the debris D separated from the lesion area A. The collection device 30 is inserted into the body lumen from the upstream side of the lesion area A and the second engagement portion 33 is engaged with the first engagement portion 12 to be collected while being pulled in the upstream direction (the first direction X) after the treatment of the lesion area A is completed. At this time, the first engagement portion 12 is positioned at the first direction X side, that is, the upstream side of the trapping portion 10. For this reason, the second engagement portion 33 of the collection shaft 31 can easily engage with the first engagement portion 12 from the upstream side and the trapping portion 10 can be pulled to the upstream side. Thus, it is possible to effectively collect the debris D trapped by the trapping portion 10 along with the trapping portion 10 by using the thick blood vessel at the upstream side of the lesion area A. The medical system 1 is particularly effective when the lesion area A is totally occluded since the conveying device 20 does not pass through the lesion area A at the time of indwelling the trapping portion 10.

The disclosure in this application is not limited to the above-described embodiment and can be modified into various forms within the technical spirit of the invention by those skilled in the art. For example, the medical system 1 may be used in a vein. The body lumen that the medical system 1 is inserted into is not limited to the blood vessel. The body lumen may be, for example, a vascular, an ureter, a bile duct, a fallopian tube, a hepatic duct, or the like. A syringe or the like may be connected to the catheter hub 37 for a sucking operation at the time of collecting the trapping portion 10 to the guiding catheter 35. Debris D which is trapped by the trapping portion 10 can accordingly be sucked by the guiding catheter 35 to be effective accommodated in the guiding catheter because negative pressure is generated in the lumen of the guiding catheter 35.

Figure 7:
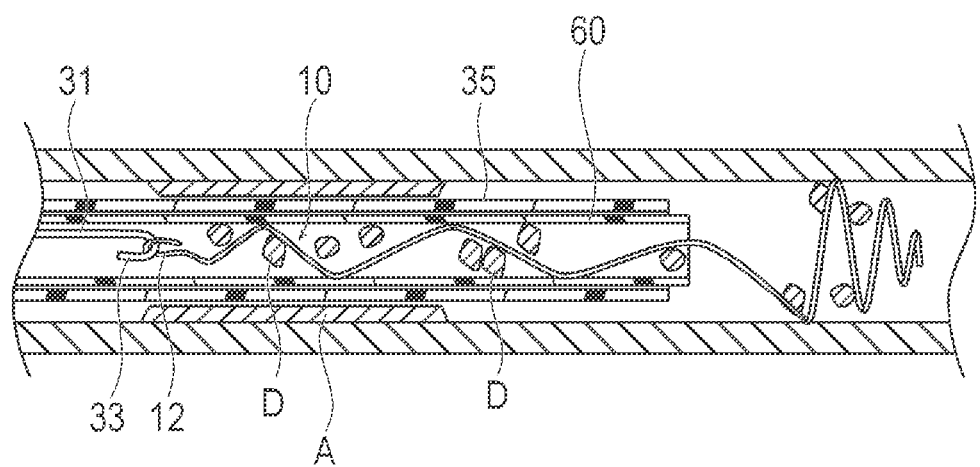
FIG. 7 is a cross-sectional view illustrating a first modified example of the medical system.

The collection pipe body 60 may not be the guiding catheter 35 as shown in a first modified example illustrated in FIG. 7. The collection pipe body 60 can be accommodated inside of a guiding catheter 35. Accordingly, the trapping portion 10 and the debris D are accommodated in the collection pipe body 60. This configuration makes it possible to remove the collection pipe body 60 accommodating the trapping portion 10 and the debris D to the outside of the body while maintaining the position of the guiding catheter 35 (i.e., the collection pipe body 60 can be removed while the guiding catheter 35 stays in place). Thus, it is possible to further perform other treatments that use the guiding catheter 35.

Figure 8A:
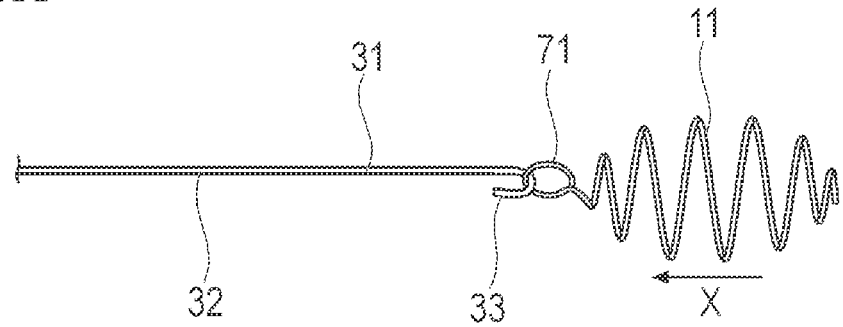
FIGS. 8A and 8B are top views illustrating a modified example of the medical system.
Figure 8B:
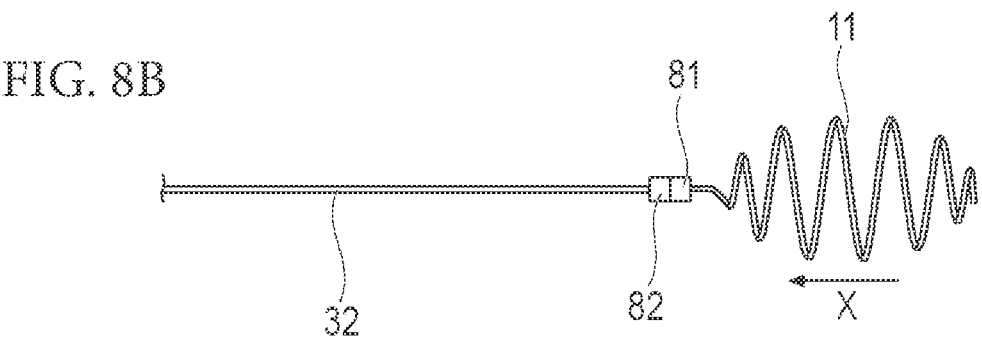

An engagement portion 71 may have an annular shape as shown in a second modified example illustrated in FIG. 8A. The same reference numerals are given to the portions having the same functions as those of the above-described embodiment(s) and a description thereof is omitted. A first engagement portion 81 and a second engagement portion 82 may be magnetic bodies as in a third modified example illustrated in FIG. 8B. In the embodiment illustrated in FIG. 8B, at least one of the first engagement portion 81 and the second engagement portion 82 is magnetic. Even in this configuration, the second engagement portion 82 can engage with the first engagement portion 81 by a magnetic force.

Figure 9A:
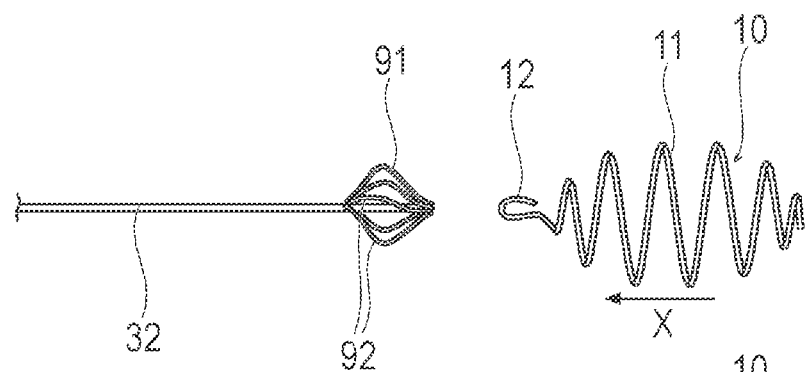
FIGS. 9A and 9B are top views illustrating a fourth modified example of the medical system.
Figure 9B:
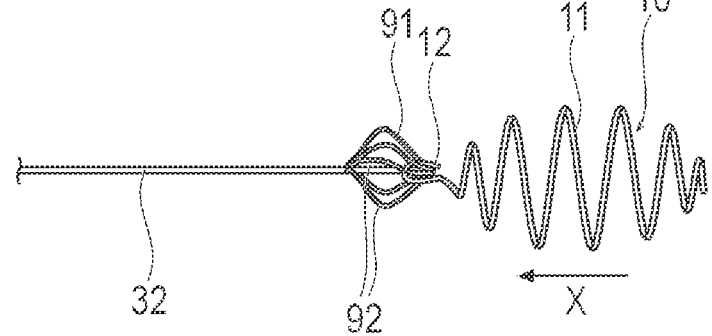

Further, a second engagement portion 91 may include a plurality of bent wires 92 as in a fourth modified example illustrated in FIG. 9A. Both ends of the wire 92 are connected to the shaft base portion 32. As illustrated in FIG. 9B, the engagement of the second engagement portion 91 can be easily performed in such a manner that at least one wire 92 is caught by (i.e., connected to or engaged with) the first engagement portion 12.

Figure 10A:
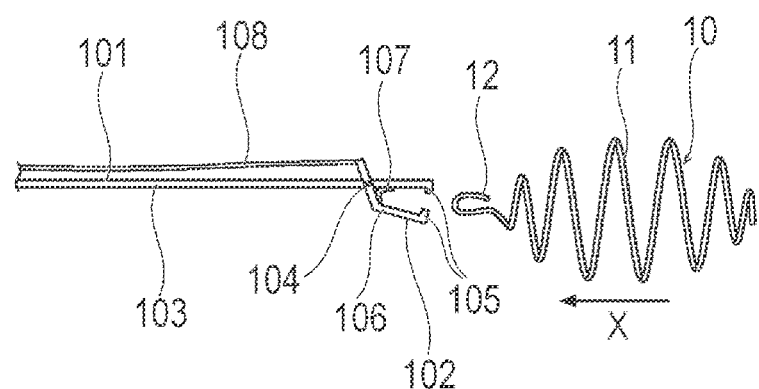
FIGS. 10A and 10B are top views illustrating a fifth modified example of the medical system.
Figure 10B:
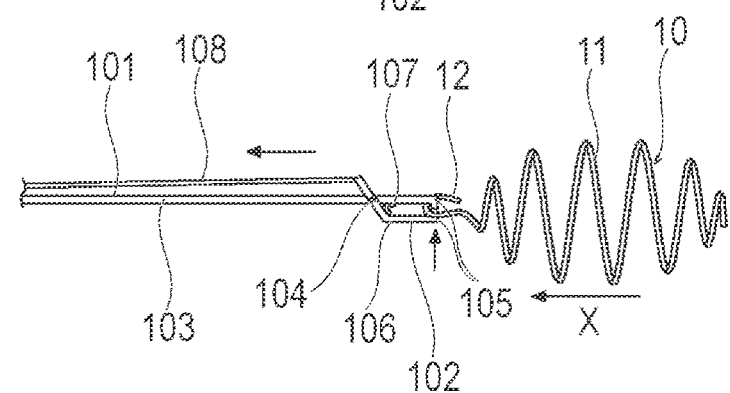

A second engagement portion 102 may include a clamp 106 which can be opened and closed by the operation at the proximal portion of a collection shaft 101 as in a fifth modified example illustrated in FIG. 10A. The clamp 106 is connected to a shaft base portion 103 by a pin 104 so that the clamp 106 is rotatable. The distal end of the clamp 106 and the distal end of the shaft base portion 103 are provided with contact portions 105 which move close to and away from each other (i.e., the contact portions 105 are moveable relative to one another to be in close proximity/contacting or to be spaced apart from one another). The proximal end of the clamp 106 is connected to an operation wire 108 extending to the proximal portion of the shaft base portion 103. The clamp 106 is urged by a leaf spring 107 to an open position when the operation wire 108 is not being pulled. When the operation wire 108 is pulled, the contact portions 105 are urged to close and the leaf spring 107 is bent as illustrated in FIG. 10B. The second engagement portion 102 can thus engage with the first engagement portion 12 so that the second engagement portion 102 sandwiches the first engagement portion 12. When the pulling of the operation wire 108 is stopped, the contact portions 105 open by the urging force of the leaf spring 107.

Figure 11A:
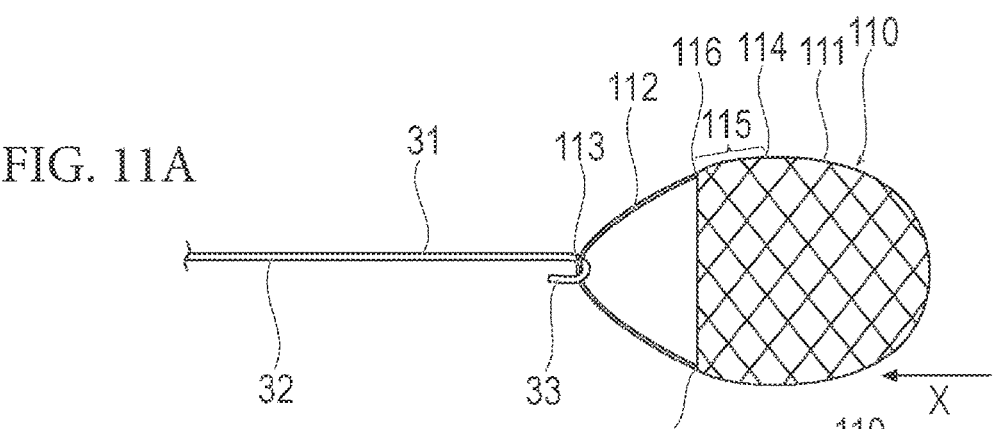
FIGS. 11A and 11B are top views illustrating a sixth modified example of the medical system.

A trapping portion 110 may include a filter portion 111 which is knitted in a cage shape as in a sixth modified example illustrated in FIG. 11A. The filter portion 111 knitted in the cage shape has liquid permeability (i.e., liquid may permeate through the filter portion 111). The trapping portion 110 includes the filter portion 111, a support wire 112 which extends to the distal side from the filter portion 111, and a first engagement portion 113 which is positioned at the distal side of the support wire 112. Since the filter portion 111 is formed by knitting an elastically deformable wire material, the filter portion 111 is formed in a cup shape having a concave portion that opens toward the distal side in an expanded state as shown in FIG. 11A. The filter portion 111 can thus effectively trap the debris D in the concave portion. Further a collection assisting portion 115 of the filter portion 111, which extends inward in the radial direction of the trapping portion 110 while extending toward the first direction X, is provided in an outer peripheral surface which extends toward the first direction X from a maximum portion 114 having a maximum outer diameter in an expanded state. The trapping portion 110 can be accommodated in the conveying pipe body 21 and in the guiding catheter 35 in a contracted state because the trapping portion 110 is an elastically deformable wire material.

The support wire 112 is one wire material (i.e., a single wire) which is fixed to two positions at the distal end of the filter portion 111. The support wire 112 is folded back at the distal side and the folded portion is the first engagement portion 113. The wire material of the filter portion 111 and the support wire 112 may be any of the materials discussed above regarding the trapping portion 10.

Figure 11B:
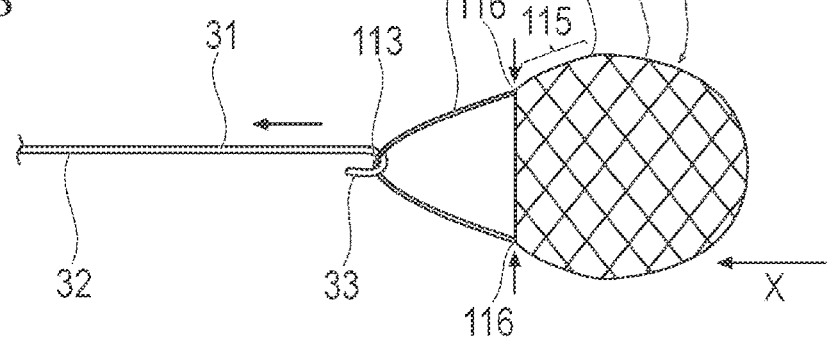

A coupling portion 116 between the support wire 112 and the filter portion 111 is positioned at the outside in the radial direction (i.e., radially outward) in relation to the first engagement portion 113. When a force is applied to the first engagement portion 113 of the trapping portion 110 in the first direction X, the end of the filter portion 111 at the first direction X side contracts inward in the radial direction as illustrated in FIG. 11B. The trapping portion 110 can thus be collected by the guiding catheter 35 (the collection pipe body) in a contracted state. The debris D trapped by the filter portion 111 is surrounded by the filter portion 111 when the filter portion 111 contracts radially inward. For this reason, the debris D can be easily collected without separation.

The outer peripheral surface of the trapping portion 110 extending toward the first direction X from the maximum portion 114 (i.e., the portion having a maximum outer diameter in an expanded state) is provided with the collection assisting portion 115 which extends inward in the radial direction of the trapping portion 110 while extending toward the first direction X. Accordingly, when the trapping portion 110 indwelled in the body lumen in the expanded state is pulled in the first direction X, the collection assisting portion 115 smoothly contacts a body tissue or the guiding catheter 35. For this reason, the trapping portion 110 is easily collected and damage to body tissue can be suppressed. The collection assisting portion 115 may be coated with a low-friction material to be relatively smooth. The low-friction material may be, for example, a fluorine-based resin material such as polytetrafluoroethylene (PTFE) and diamond-like carbon. The wire material itself positioned at the collection assisting portion 115 may be formed of a low-friction material (for example, PTFE).

Figure 12A:
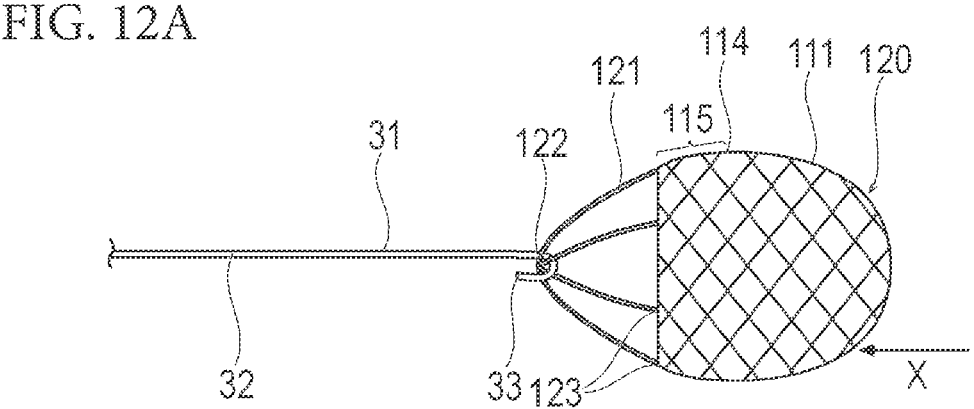
FIGS. 12A and 12B are top views illustrating a seventh modified example of the medical system.

A seventh modified example illustrated in FIG. 12A shows that a trapping portion 120 may include three or more support wires 121 (i.e., in contrast to the sixth modified example in FIG. 11A). The support wires 121 are fixed to a coupling portion 123 at the end of the filter portion 111 on the first direction X side. A portion in which the support wires 121 are brought together at the first direction X side is a first engagement portion 122. The coupling portion 123 between the support wires 121 and the filter portion 111 is positioned at the outside in the radial direction in relation to the first engagement portion 122. When a force is applied to the first engagement portion 122 of the trapping portion 120 in the first direction X, the trapping portion 120 contracts radially inward (i.e., inward in the radial direction) as in the sixth modified example. The trapping portion 120 can thus be easily collected to the guiding catheter 35 when the trapping portion 120 is pulled in the first direction X. Further, the debris D trapped by the filter portion 111 is surrounded by the filter portion 111 when the trapping portion 120 is pulled in the first direction X. The debris D can thereby be collected without separation.

Figure 12B:
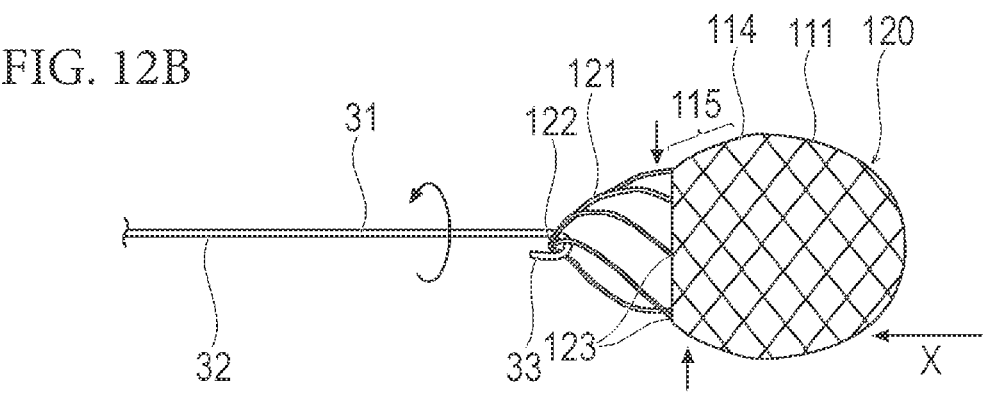

When the collection shaft 31 is rotated, a twisting force is applied to the first engagement portion 122 of the trapping portion 120. Accordingly, the end, at the first direction X side, of the filter portion 111 is contracted inward in the radial direction as illustrated in FIG. 12B. The trapping portion 120 can thus be easily collected by the guiding catheter 35 in a contracted state. The debris D trapped by the filter portion 111 is surrounded by the filter portion 111 when the filter portion 111 contracts radially inward. For this reason, the debris D can be easily collected so as not to be separated (e.g., from the filter portion 111). Additionally, in the sixth modified example illustrated in FIGS. 11A and 11B, the same effect can be obtained even when the collection shaft 31 is rotated. However, since the coupling portion 123 between the support wire 121 and the filter portion 111 is provided at three or more positions in the circumferential direction in the seventh modified example, the filter portion 111 can be stably decreased in diameter.

Figure 13A:
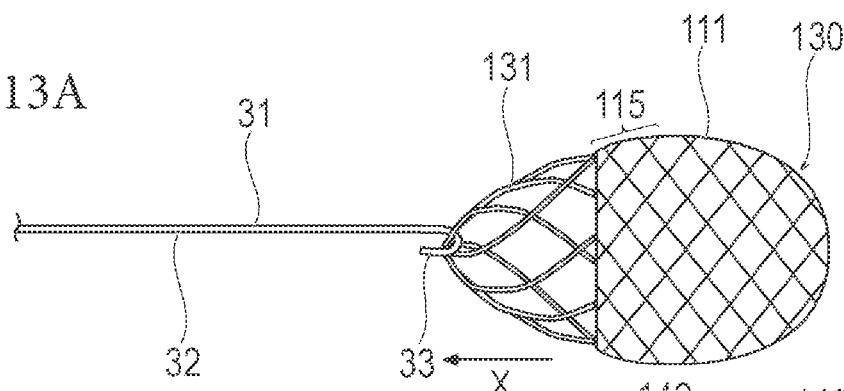
FIGS. 13A and 13B are top views illustrating a modified example of the medical system.

An eighth modified example is illustrated in FIG. 13A. FIG. 13A illustrates that a trapping portion 130 may include a mesh-shaped support wire 131 (in contrast to the sixth modified example). In addition, the mesh interval of the support wire 131 is wider than the mesh interval of the filter portion 111. Even in this configuration, the second engagement portion 33 may engage at any position (the first engagement portion) where the wire material of the support wire 131 intersects.

Figure 13B:
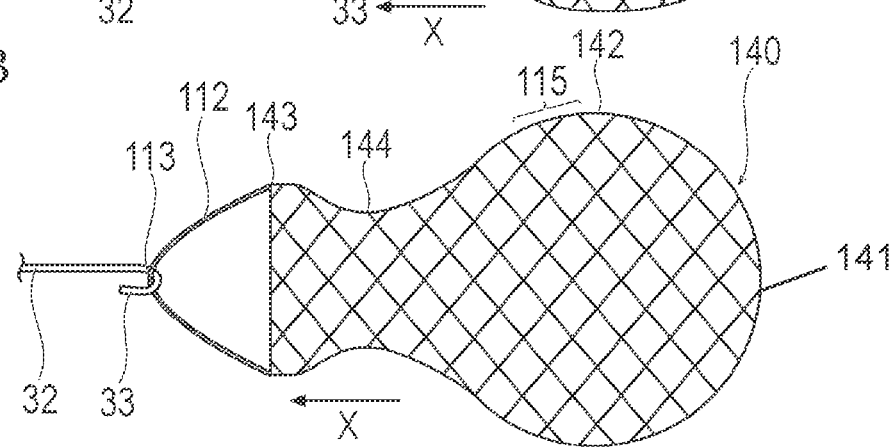

In a ninth modified example illustrated in FIG. 13B, a trapping portion 140 may include a filter portion 141 having a shape different from that of the sixth modified example. The filter portion 141 includes a contracted portion 144 which possesses an outer diameter that decreases between a maximum portion 142 (where the outer diameter becomes maximal or is the largest) and an end 143 at the first direction X side.

Figure 14A:
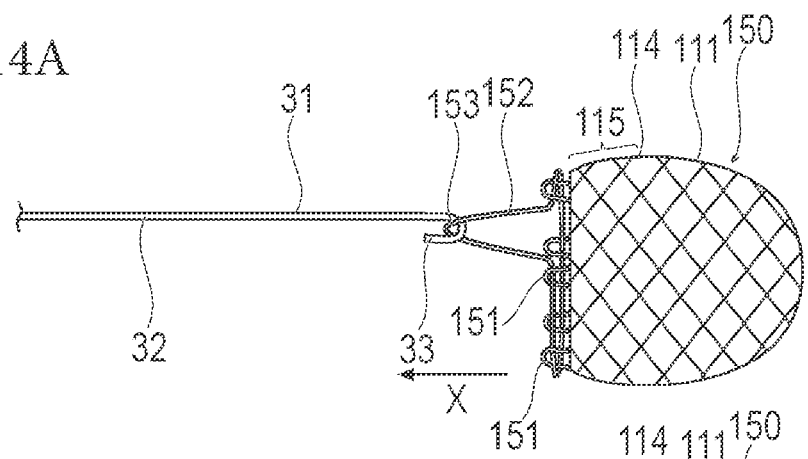
FIGS. 14A and 14B are top views illustrating a tenth modified example of the medical system.
Figure 14B:
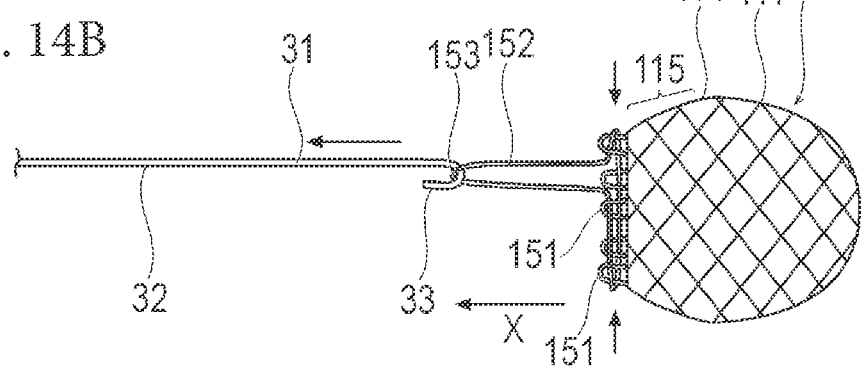

A trapping portion 150 may include the filter portion 111 which is knitted in a mesh shape, a plurality of annular portions 151 provided at the end of the filter portion 111 at the first direction X side to be parallel in the circumferential direction, and an annular support wire 152 which passes through all the annular portions 151 as shown in the tenth modified example of FIG. 14A. A portion which is formed by folding back the support wire 152 at the first direction X side becomes a first engagement portion 153. When the second engagement portion 33 is pulled while engaging with the first engagement portion 153, an entrance of a concave portion of the filter portion 111 at the first direction X side is narrowed by the support wire 152 as illustrated in FIG. 14B. Accordingly, the debris D can be easily collected without separation since the debris D which is trapped by the filter portion 111 is surrounded by the filter portion 111.

Figure 15A:
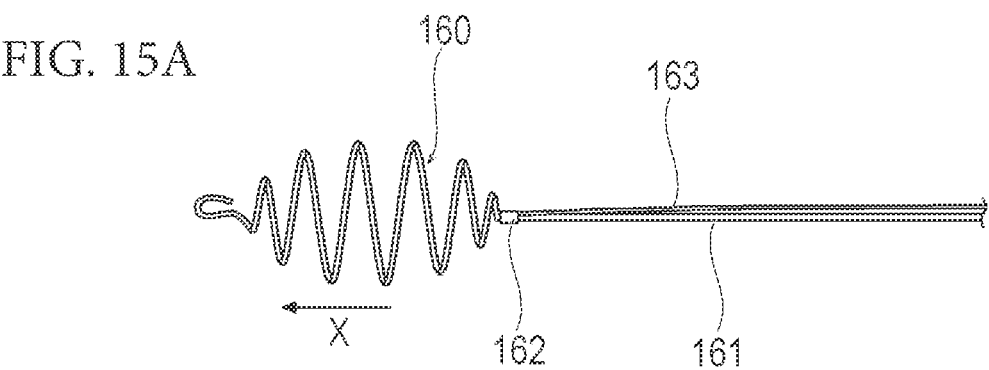
FIGS. 15A and 15B are top views illustrating a modified example of the medical system.

The eleventh modified example illustrated in FIG. 15A includes a spiral trapping portion 160 which may be a wire material and integrated with a pressing shaft 161 for pressing the trapping portion 160 from the conveying pipe body 21. When the trapping portion 160 is connected to the pressing shaft 161, the trapping portion 160 can be pressed by the pressing shaft 161 and also can be positioned in a pulled state. Accordingly, the position of the trapping portion 160 inside the blood vessel can be highly accurately set. The trapping portion 160 is fusible from the pressing shaft 161 by an electrode 162 to which a high-frequency current flows via a wire 163.

Figure 15B:
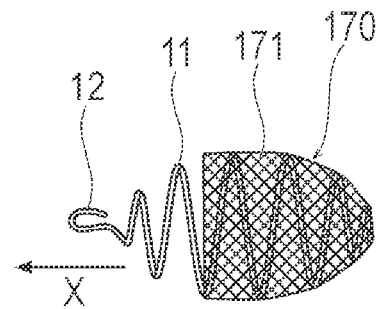

A trapping portion 170 may include a flexible mesh 171 having liquid permeability as in a twelfth modified example illustrated in FIG. 15B. The mesh 171 covers, for example, the outer peripheral surface (or the inner peripheral surface) at the downstream side of the spiral portion 11. Since the mesh 171 is provided, the debris D can be more reliably trapped.

The detailed description above describes a medical system and a method of removing an object from a living body. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method comprising:
    moving a tubular body inside a body lumen in a living body so that a distal end of the tubular body approaches a stenosed site in the body lumen from a position downstream of the stenosed site;
    indwelling a filter inside the body lumen by moving the filter from a position inside the tubular body to a position outside the tubular body such that the filter is completely removed from the tubular body, the filter being expandable and contractible, and the filter being indwelled at a position downstream from a stenosed site in the body lumen;
    moving a collection device in a downstream direction within the living body from upstream of the stenosed site to the stenosed site while the filter remains indwelled at the position downstream from the stenosed site;
    engaging the filter with the collection device while the filter is indwelled at the position downstream from the stenosed site so that the filter is connected to the collection device; and
    removing the collection device and the filter from the living body by moving both the filter and the collection device in an upstream direction while the filter and the collection device are engaged with one another.

2. The method according to claim 1, further comprising treating the stenosed site to reduce stenosis in the body lumen at the stenosed site before the removing of the collection device and the filter from the living body.

3. The method according to claim 2, wherein the treating of the stenosed site causes debris to break away from the stenosed site and flow downstream, the filter trapping the debris after the debris flows downstream.

4. The method according to claim 2, wherein the collection device is moved in the downstream direction through the stenosed site after the treating of the stenosed site so that the collection device reaches the filter before engaging the filter.

5. The method according to claim 3, wherein the filter and the debris are contained within the collection device when the collection device and the filter are moved in the upstream direction.

6. The method according to claim 1, wherein the indwelling of the filter inside the body lumen comprises:
    moving a tube within the living body, the tube containing the filter; and
    discharging the filter from the tube at the position downstream from the stenosed site, the filter expanding radially outwardly after being discharged to indwell in the body lumen.

7. The method according to claim 1, further comprising:
    moving a balloon catheter within the living body to the stenosed site in the body lumen after the indwelling of the filter, the balloon catheter comprising a balloon, the balloon being expandable radially outward from a deflated condition to an inflated condition, the balloon being in the deflated condition when the balloon catheter is moving within the living body;
    inflating the balloon of the balloon catheter at the stenosed site to the inflated condition so that the balloon contacts an inner wall of the body lumen at the stenosed site to expand an inner diameter of the stenosed site;
    deflating the balloon of the balloon catheter to the deflated condition; and
    removing the balloon catheter from the living body before the moving of the collection device within the living body.

8. The method according to claim 7, wherein the balloon catheter moves from upstream of the stenosed site to the stenosed site during the moving of the balloon catheter with the balloon in the deflated position.

9. A method comprising:
    moving a tubular body inside a body lumen in a living body so that a distal end of the tubular body approaches a stenosed site in the body lumen from a position downstream of the stenosed site;
    moving a filter positioned inside the tubular body to a position outside the tubular body such that the filter is completely removed from the tubular body, wherein the moving of the filter to the position outside the tubular body occurs while the distal end of the tubular body is positioned downstream of the stenosed site;

moving a hollow tube inside the body lumen in the living body toward the stenosed site from a position upstream of the stenosed site;

positioning the filter in a lumen in the hollow tube; and removing the hollow tube and the filter from the living body while the filter is positioned in the lumen in the hollow tube by moving both the filter and the hollow tube in an upstream direction.

10. The method according to claim 9, further comprising treating the stenosed site to reduce stenosis in the body lumen at the stenosed site before the removing of the hollow tube and the filter from the living body.

11. The method according to claim 10, wherein the hollow tube is moved in a downstream direction through the stenosed site after the treating of the stenosed site.

12. The method according to claim 10, wherein the treating of the stenosed site causes debris to break away from the stenosed site and flow downstream, the filter trapping the debris after the debris flows downstream.

13. The method according to claim 12, wherein the filter and the debris are contained within the hollow tube when the hollow tube and the filter are moved in the upstream direction.

14. The method according to claim 9, wherein the moving of the filter to the position outside the tubular body comprises pushing the filter out of the tubular body through use of a shaft positioned in the tubular body.

15. The method according to claim 9, further comprising:

moving a balloon catheter within the living body to the stenosed site in the body lumen, the balloon catheter comprising a balloon that is expandable radially outward from a deflated condition to an inflated condition, the balloon being in the deflated condition when the balloon catheter is moving within the living body;

inflating the balloon of the balloon catheter at the stenosed site to the inflated condition so that the balloon contacts an inner wall of the body lumen at the stenosed site to expand an inner diameter of the stenosed site, the filter remaining at the position outside the tubular body and downstream of the stenosed site when the balloon is inflated to the inflated condition;

deflating the balloon of the balloon catheter to the deflated condition; and removing the balloon catheter from the living body.

16. The method according to claim 15, wherein the moving of the balloon catheter within the living body to the stenosed site while the balloon is in the deflated condition comprises moving the balloon catheter in a downstream direction toward the stenosed site.

17. A method comprising:

moving a tubular body inside a body lumen in a living body so that a distal end of the tubular body approaches a stenosis in the body lumen from a position downstream of the stenosis;

positioning a spiral-shaped wire that is expandable and contractible in the body lumen from a position inside the tubular body to a position outside the tubular body such that the spiral-shaped wire is completely removed from the tubular body and is at a position downstream from the stenosis in the body lumen;

treating the stenosis while the spiral-shaped wire remains positioned downstream from the stenosis to enlarge a passage through the stenosis;

trapping debris resulting from the treating of the stenosis in the spiral-shaped wire;

moving the spiral-shaped wire that is positioned downstream from the stenosis in an upstream direction so that the spiral-shaped wire passes through the passage in the stenosis after the treating of the stenosis, the moving of the spiral-shaped wire in the upstream direction including moving the debris trapped in the spiral-shaped wire; and removing the spiral-shaped wire and the debris trapped in the spiral-shaped wire from the living body after the spiral-shaped wire passes through the passage in the stenosis.

18. The method according to claim 17, wherein the moving of the spiral-shaped wire in the upstream direction so that the spiral-shaped wire passes through the passage in the stenosis comprises:

positioning the spiral-shaped wire in a lumen of a tube; and moving both the tube and the spiral-shaped wire positioned in the lumen of the tube in the upstream direction.

19. The method according to claim 17, further comprising:

moving a tube in the body lumen in the living body so that a distal end of the tube approaches the stenosis from upstream of the stenosis while a collection shaft is positioned in a lumen in the tube; and causing a distal end of the collection shaft to engage the spiral-shaped wire that is positioned downstream from the stenosis; and pulling the spiral-shaped wire into the lumen in the tube by relatively moving the tube and the collection shaft so that the distal end of the collection shaft moves in the upstream direction relative to the tube.

20. The method according to claim 17, wherein the positioning of the spiral-shaped wire in the body lumen comprises:

moving a tubular body in the upstream direction towards the stenosis and positioning a distal end of the tubular body downstream from the stenosis while the spiral-shaped wire is positioned inside the tubular body;

discharging the spiral-shaped wire from the distal end of the tubular body to position the spiral-shaped wire downstream from the stenosis; and removing the tubular body from the living body while the spiral-shaped wire remains positioned downstream from the stenosis.

\* \* \* \* \*